(12) United States Patent
Serban et al.

(10) Patent No.: US 9,024,097 B2
(45) Date of Patent: *May 5, 2015

(54) INTEGRATED HYDROGENATION/DEHYDROGENATION REACTOR IN A CATALYTIC REFORMING PROCESS CONFIGURATION FOR IMPROVED AROMATICS PRODUCTION

(75) Inventors: Manuela Serban, Glenview, IL (US); Kurt M. VandenBussche, Lake in the Hills, IL (US); Mark D. Moser, Elk Grove Village, IL (US); David A. Wegerer, Lisle, IL (US)

(73) Assignee: UOP LLC, Des Plaines, IL (US)

( * ) Notice: Subject to any disclaimer, the term of this patent is extended or adjusted under 35 U.S.C. 154(b) by 143 days.

This patent is subject to a terminal disclaimer.

(21) Appl. No.: 13/327,192

(22) Filed: Dec. 15, 2011

(65) Prior Publication Data

US 2013/0158313 A1   Jun. 20, 2013

(51) Int. Cl.
| | | |
|---|---|---|
| *C10G 35/04* | (2006.01) | |
| *C07C 5/02* | (2006.01) | |
| *C07C 5/41* | (2006.01) | |
| *C07C 15/04* | (2006.01) | |
| *C07C 15/06* | (2006.01) | |
| *C10G 35/085* | (2006.01) | |
| *C10G 35/095* | (2006.01) | |
| *C10G 35/24* | (2006.01) | |
| *C10G 59/02* | (2006.01) | |

(52) U.S. Cl.
CPC . *C07C 5/41* (2013.01); *C07C 15/04* (2013.01); *C07C 15/06* (2013.01); *C10G 35/04* (2013.01); *C10G 35/085* (2013.01); *C10G 35/095* (2013.01); *C10G 35/24* (2013.01); *C10G 59/02* (2013.01); *C10G 2400/30* (2013.01)

(58) Field of Classification Search
CPC .............. C07C 5/00; C07C 5/02; C07C 5/03; C07C 5/32; C07C 5/321; C07C 5/324; C07C 3/325; C07C 4/00; C07C 4/02; C07C 4/04; C07C 4/06; C10G 35/00; C10G 35/02; C10G 35/04; C10G 35/06; C10G 35/085; C10G 35/09
USPC ......... 585/251, 300–304, 312, 315, 319, 322, 585/407, 430, 800, 804, 805
See application file for complete search history.

(56) References Cited

U.S. PATENT DOCUMENTS

| | | | | |
|---|---|---|---|---|
| 2,528,693 | A * | 11/1950 | Johnson ..................... | 585/256 |
| 2,937,132 | A * | 5/1960 | Voorhies, Jr. ................. | 208/64 |
| 3,647,680 | A * | 3/1972 | Greenwood et al. ............ | 208/65 |
| 4,401,554 | A * | 8/1983 | Choi et al. ....................... | 208/64 |

(Continued)

OTHER PUBLICATIONS

Sinnott, R.K. (2005). Coulson and Richardson's Chemical Engineering vol. 6—Chemical Engineering Design (4th Edition) . . . Elsevier.*

(Continued)

*Primary Examiner* — In Suk Bullock
*Assistant Examiner* — Philip Louie

(57) ABSTRACT

A process for reforming hydrocarbons is presented. The process involves applying process controls over the reaction temperatures to preferentially convert a portion of the hydrocarbon stream to generate an intermediate stream, which will further react with reduced endothermicity. The intermediate stream is then processed at a higher temperature, where a second reforming reactor is operated under substantially isothermal conditions.

13 Claims, 1 Drawing Sheet

(56) References Cited

U.S. PATENT DOCUMENTS

| | | | |
|---|---|---|---|
| 4,914,075 A | | 4/1990 | Bricker et al. |
| 5,935,415 A | * | 8/1999 | Haizmann et al. ............. 208/64 |
| 6,004,452 A | * | 12/1999 | Ash et al. ...................... 208/80 |
| 2007/0299289 A1 | * | 12/2007 | Bresler et al. ................ 585/323 |

OTHER PUBLICATIONS

Shepard, A. F., A. L. Henne, and T. Midgley. "Physical properties of the normal paraffin hydrocarbons, pentane to dodecane." Journal of the American Chemical Society 53.5 (1931): 1948-1951.*

U.S. Appl. No. 13/327,164, filed Dec. 15, 2011, Moser et al.
U.S. Appl. No. 13/327,200, filed Dec. 15, 2011, Moser et al.
U.S. Appl. No. 13/327,143, filed Dec. 15, 2011, Moser et al.
U.S. Appl. No. 13/327,212, filed Dec. 15, 2011, Moser et al.
U.S. Appl. No. 13/327,220, filed Dec. 15, 2011, Moser et al.
U.S. Appl. No. 13/327,178, filed Dec. 15, 2011, Serban et al.
U.S. Appl. No. 13/327,170, filed Dec. 15, 2011, Serban et al.
U.S. Appl. No. 13/327,185, filed Dec. 15, 2011, Serban et al.

* cited by examiner

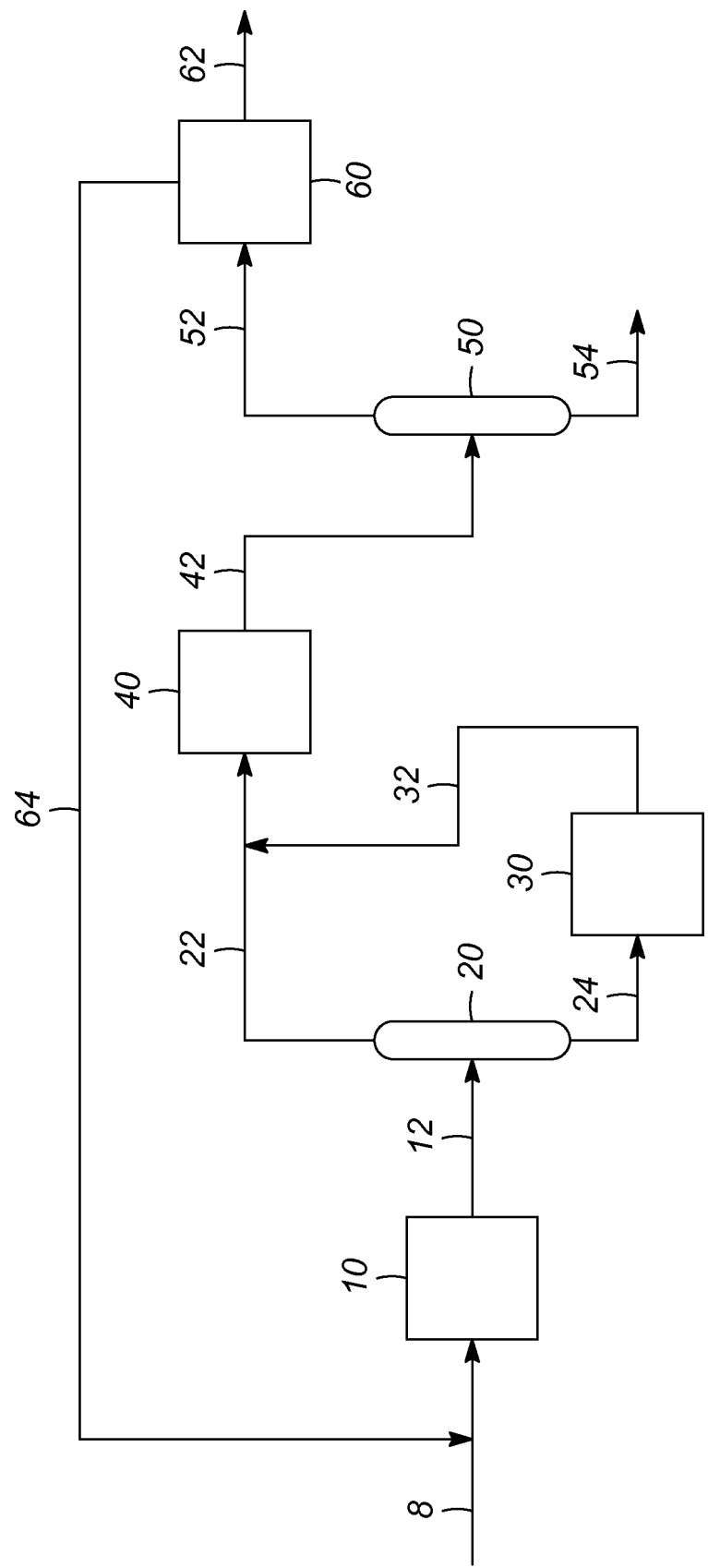

INTEGRATED HYDROGENATION/DEHYDROGENATION REACTOR IN A CATALYTIC REFORMING PROCESS CONFIGURATION FOR IMPROVED AROMATICS PRODUCTION

FIELD OF THE INVENTION

The present invention relates to the process of enhancing the production of aromatic compounds. In particular the improvement and enhancement of aromatic compounds such as benzene, toluene and xylenes from a naphtha feedstream.

BACKGROUND OF THE INVENTION

The reforming of petroleum raw materials is an important process for producing useful products. One important process is the separation and upgrading of hydrocarbons for use as a motor fuel or upgrading the octane value of the naphtha in the production of gasoline. However, hydrocarbon feedstreams from a raw petroleum source also include useful chemical precursors for use in the production of plastics, detergents and other products.

The upgrading of gasoline is an important process, and improvements for the conversion of naphtha feedstreams to increase the octane number have been presented in U.S. Pat. Nos. 3,729,409, 3,753,891, 3,767,568, 4,839,024, 4,882,040 and 5,242,576. These processes involve a variety of means to enhance octane number, and particularly for enhancing the aromatic content of gasoline.

While there is a move to reduce the aromatics in gasoline, aromatics have many important commercial uses. Among them are the production of detergents in the form of alkyl-aryl sulfonates, and plastics. These commercial uses require more and purer grades of aromatics. The production and separation of aromatics from hydrocarbons streams is, therefore, increasingly important.

Processes include splitting feeds and operating several reformers using different catalysts, such as a monometallic catalyst or a non-acidic catalyst for lower boiling point hydrocarbons and bi-metallic catalysts for higher boiling point hydrocarbons. Other improvements include new catalysts, as presented in U.S. Pat. Nos. 4,677,094, 6,809,061 and 7,799,729. However, there are limits to the methods and catalysts presented in these patents which can entail significant increases in costs.

Improved processes are needed to reduce the costs and energy usage in the production of aromatic compounds.

SUMMARY OF THE INVENTION

A process for reforming hydrocarbons is presented. The process involves applying process controls over the reaction temperatures to preferentially convert a portion of the hydrocarbon stream to generate an intermediate stream, and to separate the intermediate stream into separate fractions for processing. A portion of the intermediate stream is then processed at a higher temperature, where a high temperature reforming reactor system is operated under substantially isothermal conditions.

The process for producing aromatic compounds from a hydrocarbon feedstream includes passing the hydrocarbon feedstream to a hydrogenation/dehydrogenation reactor system to generate a first stream. The first stream has a composition with a reduced amount of hydrocarbons, which would react with high endothermicity in the reforming process. The first stream is passed to a fractionation unit to generate an overhead stream comprising C7 and lighter paraffins, and a bottoms stream comprising heavier paraffins. The overhead stream is passed to a high temperature reforming reactor system to generate a reformate product stream comprising C6 and C7 aromatics.

In an alternate embodiment, the process further includes passing the bottoms stream to a second reforming reactor system, to generate a second effluent stream. The second effluent stream is then passed to the high temperature reforming reactor system, where the stream undergoes further reforming to increase the C6 and C7 aromatics.

Other objects, advantages and applications of the present invention will become apparent to those skilled in the art from the following detailed description and drawings.

BRIEF DESCRIPTION OF THE DRAWING

The FIGURE is a diagram of a process for increasing aromatics yields by reducing naphthenic and olefinic compounds prior to processing the hydrocarbons at a high temperature.

DETAILED DESCRIPTION OF THE INVENTION

There is an increased demand for aromatics. Important aromatics include benzene, toluene, and xylenes. These aromatics are important components in the production of detergents, plastics, and other high value products. With increasing energy costs, energy efficiency is an important aspect for improving the yields of aromatics. The present invention provides for understanding the differences in the properties of the different components in a hydrocarbon mixture to develop a better process.

A hydrocarbon stream is comprised of many constituents, and each constituent behaves differently under different conditions. The constituents can be divided into larger classes of compounds, where one class, such as paraffins, comprises many different paraffinic compounds. The dehydrogenation process is an endothermic process which requires a continuous input of energy to heat the process stream in the reactor. The greater the endothermicity, the greater the temperature drop within the reactor, and therefore the greater the amount of heat that is to be added to maintain the reaction. The dropping of temperature reduces the reaction rate and reduces the conversion. This requires additional heat to maintain a desired reaction rate.

Among the constituents in the hydrocarbon stream, the amount of endothermicity varies considerably. Energy usage in the dehydrogenation process can be reduced by separating out the individual constituents, but would be increased in the endeavor to separate the constituents. However, the reaction rates for the different constituents, and for the different classes of compounds varies. These variations change with temperature, such that different reactions, and different operating temperatures allow for a partial selectivity of the dehydrogenation process over some constituents and classes of compounds.

Compounding problems in the dehydrogenation process are the conversion rates for some of the constituents. In order to achieve good conversion of C6 and C7 paraffins to aromatic compounds, high temperatures and relatively short contact times are required. With the high endothermicity, control and maintenance of high reaction temperatures can be difficult. The hydrocarbon stream of primary interest is a full boiling range naphtha having olefins, naphthenes, paraffins, and aromatics, and the process is aimed at converting the non-aromatics to higher value aromatic compounds.

In particular, the compounds with the greatest endothermicity include naphthenes. It has been found that operating different reactors at different conditions can improve aromatic yields by passing the hydrocarbon process stream sequentially through the different reactors.

The process of the present invention has found that converting naphthenic compounds and olefinic compounds before dehydrogenation and cyclization of paraffins can yield an increase in aromatic compounds, and especially an increase in benzene, toluenes and xylenes. The process, as shown in the FIGURE, comprises passing a hydrocarbon stream 8 to a hydrogenation/dehydrogenation reactor unit 10. The reactor unit 10 is operated at appropriate reaction conditions to hydrogenate olefins and to dehydrogenate naphthenes, to generate a first stream 12 with a reduced olefin and naphthene content. The first stream 12 is passed to a first fractionation unit 20 to generate an overhead stream 22 comprising C7 and lighter paraffins, and a bottoms stream 24 comprising heavier hydrocarbons. The overhead stream 22 is passed to a high temperature reforming reactor system 40 to generate a reformate product stream 42.

The process can further include processing the bottoms stream 24, where the bottoms stream 24 is passed to a low temperature reforming reactor system 30 to generate a first reformer effluent stream 32. The first reformer effluent stream 32 is passed to the high temperature reformer 40 for further conversion of paraffins within the effluent stream 32.

The reformate product stream 42 can be passed to a reformate splitter 50 to generate a reformate splitter overhead stream 52 comprising C6 and C7 aromatics, and a bottoms stream 54. The reformate overhead stream 52 is passed to an aromatics recovery unit 60 thereby generating an aromatics product stream 62 comprising benzene and toluene. The aromatics recovery unit additionally generates a raffinate stream 64 comprising paraffins. One industry standard for an aromatics recovery unit 60 is the Sulfolane™ process, which is an extractive distillation process utilizing sulfolane to facilitate high purity extraction of aromatics. The Sulfolane™ process is well known to those skilled in the art.

In an alternative arrangement, the raffinate stream 64 can be passed to a naphtha hydrotreater (not shown) to remove residual sulfur compounds that can be picked up from the aromatics recovery unit 60. The process can also include passing the hydrocarbon feedstream to a naphtha hydrotreater before passing the hydrocarbon stream to the hydrogenation/dehydrogenation unit 10.

In one embodiment, the raffinate stream 64 can be passed to the hydrogenation/dehydrogenation unit 10 for conversion of olefins generated in the reforming reactor systems 30, 40.

The hydrogenation/dehydrogenation reactor system 10 uses a single catalyst. The catalyst is a non-acidic catalyst and has a metal function. The preferred catalyst is a metal deposited on an inert support. The catalyst is non-chlorided. The catalyst performs two functions, while it is a single catalyst. In studying the reaction rates of various classes of hydrocarbons, the various classes of hydrocarbons were looked at for catalytic reactions over a catalyst with a platinum metal. For hydrogenation the reaction rates run from about $10^{-2}$ to $10^2$ molecules/site-s, and has an operating window generally from 200° C. to 450° C. Dehydrogenation has reaction rates from about $10^{-3}$ to 10 molecules/site-s, and has an operating window generally from 425° C. to 780° C. There is an overlap of these reaction windows where both reactions occur when the temperature in the reactor is held to between 400° C. and 500° C., and preferably 420° C. and 460° C., and more preferably between 425° C. and 450° C. A wider range can be employed depending on the relative amounts of naphthenes and olefins. This allows for the simultaneous reactions of hydrogenation of some hydrocarbon components, while dehydrogenating other hydrocarbon components. In particular, olefins present can be hydrogenated while naphthenes are dehydrogenated.

In one embodiment, the hydrogenation/dehydrogenation reactor system 10 is a fixed bed reactor system, but it is intended to include other types of reactor bed structures within this invention, including, but not limited to, moving bed systems, bubbling bed systems, and stirred reactor bed systems. For a fixed bed reactor system, the process can comprise at least two reactors, where one reactor is off-line and the catalyst can undergo regeneration, while the other reactors are on-line.

The catalyst in the hydrogenation/dehydrogenation reactor system 10 is preferably a metal only catalyst on a support, where the choice of catalyst metal is from a Group VIII noble elements of the periodic table. The Group VIII noble metal may be selected from the group consisting of platinum, palladium, iridium, rhodium, osmium, ruthenium, or mixtures thereof. Platinum, however, is the preferred Group VIII noble metal component. It is believed that substantially all of the Group VIII noble metal component exists within the catalyst in the elemental metallic state. Preferably, the catalyst in the hydrogenation/dehydrogenation reactor has no acid function.

Preferably the Group VIII noble metal component is well dispersed throughout the catalyst. It generally will comprise about 0.01 to 5 wt. %, calculated on an elemental basis, of the final catalytic composite. Preferably, the catalyst comprises about 0.1 to 2.0 wt. % Group VIII noble metal component, especially about 0.1 to about 2.0 wt. % platinum.

The Group VIII noble metal component may be incorporated in the catalytic composite in any suitable manner such as, for example, by coprecipitation or cogelation, ion exchange or impregnation, or deposition from a vapor phase or from an atomic source or by like procedures either before, while, or after other catalytic components are incorporated. The preferred method of incorporating the Group VIII noble metal component is to impregnate the support with a solution or suspension of a decomposable compound of a Group VIII noble metal. For example, platinum may be added to the support by commingling the latter with an aqueous solution of chloroplatinic acid. Another acid, for example, nitric acid or other optional components, may be added to the impregnating solution to further assist in evenly dispersing or fixing the Group VIII noble metal component in the final catalyst composite.

The support can include a porous material, such as an inorganic oxide or a molecular sieve, and a binder with a weight ratio from 1:99 to 99:1. The weight ratio is preferably from about 1:9 to about 9:1. Inorganic oxides used for support include, but are not limited to, alumina, magnesia, titania, zirconia, chromia, zinc oxide, thoria, boria, ceramic, porcelain, bauxite, silica, silica-alumina, silicon carbide, clays, crystalline zeolitic aluminasilicates, and mixtures thereof. Porous materials and binders are known in the art and are not presented in detail here.

The high temperature reactor system 40 is to be operated as a substantially isothermal system, where the system can comprises a plurality of reactors with heaters to bring the reactor feed temperature up to the inlet temperature. For purposes of this invention, the reactor temperatures referred to are the reactor inlet temperatures. The substantially isothermal system is operated to minimize the endotherm of each reactor in the high temperature reactor system 40. The process of reacting naphthenes and olefins in the hydrogenation/dehydrogenation reactor 10 facilitates reducing the size of the endotherms in the high temperature reactors.

The high temperature reactor system 40 utilizes a reforming catalyst and is operated at a temperature between 520° C. and 600° C., with a preferred operating temperature between 540° C. and 560° C., with the reaction conditions controlled to maintain the isothermal reactions at or near 540° C. A plurality of reactor with inter-reactor heaters provides for setting the reaction inlet temperatures to a narrow range, and multiple, smaller reactors allow for limiting the residence time and therefore limiting the temperature variation across the reactor system 40. The process or reforming also includes a space velocity between 0.6 hr$^{-1}$ and 10 hr$^{-1}$. Preferably the space velocity is between 0.6 hr$^{-1}$ and 8 hr$^{-1}$, and more preferably, the space velocity is between 0.6 hr$^{-1}$ and 5 hr$^{-1}$. Due to the elevated temperature, the problems of potential increased thermal cracking are addressed by having a shorter residence time of the process stream in the isothermal reactor system 40. An aspect of the process can use a reactor with an internal coating made of a non-coking material. The non-coking material can comprise an inorganic refractory material, such as ceramics, metal oxides, metal sulfides, glasses, silicas, and other high temperature resistant non-metallic materials. The process can also utilize piping, heater internals, and reactor internals using a stainless steel having a high chromium content. Stainless steels having a chromium content of 17% or more have a reduced coking ability.

Reforming catalysts generally comprise a metal on a support. The support can include a porous material, such as an inorganic oxide or a molecular sieve, and a binder with a weight ratio from 1:99 to 99:1. The weight ratio is preferably from about 1:9 to about 9:1. Inorganic oxides used for support include, but are not limited to, alumina, magnesia, titania, zirconia, chromia, zinc oxide, thoria, boria, ceramic, porcelain, bauxite, silica, silica-alumina, silicon carbide, clays, crystalline zeolitic aluminasilicates, and mixtures thereof. Porous materials and binders are known in the art and are not presented in detail here. The metals preferably are one or more Group VIII noble metals, and include platinum, iridium, rhodium, and palladium. Typically, the catalyst contains an amount of the metal from about 0.01% to about 2% by weight, based on the total weight of the catalyst. The catalyst can also include a promoter element from Group IIIA or Group IVA. These metals include gallium, germanium, indium, tin, thallium and lead.

The process can utilize a moving bed reactor system, where a catalyst is fed to the reactors and spent catalyst is passed to a regenerator. In one embodiment, the process passes regenerated catalyst through the second reforming reactor system 30, thereby generating a first catalyst stream. A second regenerated catalyst stream is passed to the high temperature.

In another embodiment, the regenerated catalyst is passed to the second reforming catalyst system 30 to generate a first catalyst stream. The first catalyst stream is passed to the high temperature reforming reactor system 40 to generate a second catalyst stream, and the second catalyst stream is passed to the regenerator. This process includes a heater to raise the temperature of the first catalyst stream to the inlet temperature of the high temperature reforming reactor system 40.

In yet another embodiment, the regenerated catalyst is passed through the high temperature reforming reactor system 40, to generate a high temperature catalyst effluent stream. The high temperature catalyst effluent stream is passed to the second reforming reactor system 30 to generate a low temperature catalyst effluent stream, and passing the low temperature catalyst effluent stream to the regenerator. This embodiment can take advantage of the heat in the catalyst from the high temperature system 40 to use without additional heating of the catalyst in passing to the low temperature system 30.

Therefore, increases can be achieved through innovative flow schemes that allow for process control of the reactions. While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for producing aromatic compounds from a hydrocarbon feedstream, comprising:
    passing the hydrocarbon feedstream to a hydrogenation/dehydrogenation reactor system and contacting with a hydrogenation/dehydrogenation catalyst consisting of a noble metal on a support thereby generating a first stream with reduced naphthene and olefin content, wherein the hydrogenation/dehydrogenation reactor system is operated at a temperature between 420° C. and 460° C.;
    passing the first stream to a fractionation unit to generate an overhead stream comprising C7 and lighter paraffins, and a bottoms stream comprising heavier hydrocarbons;
    passing the overhead stream to a high temperature reforming reactor system thereby generating a reformate product stream, wherein the high temperature reforming reactor system is operated at a temperature between 540° C. and 580° C.; and
    passing the bottoms stream to a second reforming reactor system, thereby generating a second effluent stream; and
    passing the second effluent stream to the high temperature reforming reactor system.

2. The process of claim 1 further comprising passing the reformate product stream to a reformate splitter, thereby generating a reformate overhead stream comprising C6 and C7 aromatics, and a bottoms stream.

3. The process of claim 2 further comprising passing the reformate overhead stream to an aromatics recovery unit thereby generating an aromatics product stream comprising benzene and toluene, and a raffinate stream.

4. The process of claim 3 further comprising passing the raffinate stream to the hydrogenation/dehydrogenation unit.

5. The process of claim 1 wherein the reforming reactor system comprises a plurality of reactors with inter-reactor heaters.

6. The process of claim 1 wherein the hydrogenation/dehydrogenation reactor system is operated at a temperature between 425° C. and 450° C.

7. The process of claim 1 wherein the feedstream is a full boiling range naphtha.

8. The process of claim 1 further comprising:
    passing regenerated catalyst through the second reforming reactor system, thereby generating a first catalyst stream;
    passing regenerated catalyst to the high temperature reforming reactor system, thereby generating a second catalyst stream; and
    passing the first catalyst stream and the second catalyst stream to a catalyst regenerator.

9. The process of claim 1 further comprising:
    passing regenerated catalyst through the high temperature reforming reactor system, thereby generating a high temperature catalyst effluent stream; and passing the high temperature catalyst effluent stream to the second reforming reactor system, thereby generating a low temperature catalyst effluent stream.

10. A process for producing aromatic compounds from a hydrocarbon feedstream, comprising:
   passing the hydrocarbon feedstream to a hydrogenation/dehydrogenation reactor system and contacting with a hydrogenation/dehydrogenation catalyst consisting of a noble metal on a support thereby generating a first stream with reduced naphthene and olefin content, wherein the hydrogenation/dehydrogenation reactor system is operated at a temperature between 420° C. and 460° C.;
   passing the first stream to a fractionation unit to generate an overhead stream comprising C7 and lighter paraffins, and a bottoms stream comprising heavier hydrocarbons and aromatics;
   passing the overhead stream to a high temperature reforming reactor system thereby generating a reformate product stream, operated at an inlet temperature between 540° C. and 580° C.;
   passing the bottoms stream to a second reforming reactor system, thereby generating a second effluent stream;
   passing the second effluent stream to the high temperature reforming reactor system;
   passing a catalyst stream to the high temperature reforming reactor system, thereby generating a first catalyst effluent stream; and
   passing the first catalyst effluent stream to a regenerator.

11. The process of claim 10 further comprising:
   passing the reformate product stream to a reformate splitter to generate a reformate overhead stream comprising C6 and C7 aromatics, and a reformate bottoms stream comprising C8 and heavier aromatics and hydrocarbons; and
   passing the reformate overhead stream to an aromatics recovery unit, thereby generating an aromatics product stream comprising benzene and toluene, and a raffinate stream.

12. The process of claim 11 further comprising passing the raffinate stream to the hydrogenation/dehydrogenation reactor.

13. The process of claim 11 further comprising;
   passing the hydrocarbon feedstream to a naphtha hydrotreater to generate a treated naphtha stream;
   passing the raffinate stream to the naphtha hydrotreater; and
   passing the treated naphtha stream and the treated raffinate stream to the hydrogenation/dehydrogenation reactor.

* * * * *